United States Patent [19]

Do-huu et al.

[11] Patent Number: 4,586,512

[45] Date of Patent: May 6, 1986

[54] DEVICE FOR LOCALIZED HEATING OF BIOLOGICAL TISSUES

[75] Inventors: Jean-Paul Do-huu; Pierre Hartemann, both of Paris, France

[73] Assignee: Thomson-CSF, Paris, France

[21] Appl. No.: 717,465

[22] Filed: Mar. 27, 1985

Related U.S. Application Data

[63] Continuation of Ser. No. 392,242, Jun. 25, 1982.

[30] Foreign Application Priority Data

Jun. 26, 1981 [FR] France .............................. 81 12612
Mar. 19, 1982 [FR] France .............................. 82 04747

[51] Int. Cl.⁴ .......................................... A61B 10/00
[52] U.S. Cl. ................................................ 128/660
[58] Field of Search ................ 128/24 A, 303.1, 362, 128/399, 401, 660; 310/334–337, 367, 369

[56] References Cited

U.S. PATENT DOCUMENTS

| | | | |
|---|---|---|---|
| 2,415,832 | 2/1947 | Mason | 171/327 |
| 2,789,557 | 4/1957 | Davis | 128/24 |
| 2,875,355 | 2/1959 | Petermann | 310/9.5 |
| 3,854,060 | 12/1974 | Cook | 310/367 |
| 4,101,795 | 7/1978 | Fukomoto et al. | 128/660 |
| 4,155,259 | 5/1979 | Engeler | 128/660 |
| 4,207,772 | 6/1980 | Stoller | 128/660 |
| 4,217,516 | 8/1980 | Iinuma et al. | 128/660 |
| 4,237,902 | 12/1980 | Okazaki | 128/660 |
| 4,241,611 | 12/1980 | Specht et al. | 128/660 |
| 4,248,090 | 2/1981 | Glenn | 128/660 |
| 4,254,662 | 4/1981 | Kuroda et al. | 128/660 |
| 4,271,948 | 7/1980 | Smith et al. | 310/334 |
| 4,368,410 | 1/1983 | Hance et al. | 128/24 A |
| 4,398,116 | 8/1983 | Louis | 310/367 |

OTHER PUBLICATIONS

"Production of Deep Focal Lesions by Focused Ultrasound–Current Status," by Lele, Ultrasonics, Apr. 1967.

Primary Examiner—Edward M. Coven
Assistant Examiner—Max F. Hindenburg
Attorney, Agent, or Firm—Cushman, Darby and Cushman

[57] ABSTRACT

A device for therapeutic heating by hyperthermia comprises an emitter which focuses ultrasonic radiation into biological tissues and produces localized heating, especially for the treatment of tumors. The radiation emitter consists of a piezoelectric plate subdivided into annular radiating zones of equal width by a set of concentric circular grooves.

27 Claims, 10 Drawing Figures

DEVICE FOR LOCALIZED HEATING OF BIOLOGICAL TISSUES

This is a continuation of application Ser. No. 392,242, filed June 25, 1982.

This invention relates to the use of heat as a therapeutic agent which can be applied locally to deep biological tissues. It is known that heating of a biological tissue entails the need to utilize energy which cannot be supplied simply by heat conduction through the body. It is therefore necessary to transfer energy to the zone to be heated by means of radiation which converges towards said zone. This accordingly prevents heating of tissues which are traversed by the radiation between the emissive surface and the focusing zone. The use of very-high-frequency electromagnetic radiation makes it possible to obtain good focusing with an applicator of reasonable size but the depth of penetration is insufficient to treat deep tissues by hyperthermia. Electromagnetic radiations of lower frequency are capable of penetrating to a greater depth in the human body but the part subjected to heating comprises all the tissues which are located in the irradiated region.

It is known that biological tissues contain a large quantity of water and are permeable to ultrasonic radiations having short wavelengths. A supply of heat which is localized in depth can therefore be provided by means of an ultrasonic radiation emitter of small size which need only be applied against the patient via a water bag. This method of treatment does not entail any need for implantation of electrodes in order to produce localized heating, thereby endowing the method with a non-traumatic character.

The applicator can be of particularly simple design and excitation of this device by means of electric signals which can readily be modulated in phase and in amplitude provides considerable flexibility in the method of treatment by hyperthermia.

The object of the invention is to provide a device for localized heating of biological tissues by projection of ultrasonic radiation by means of an electromechanical transducer associated with an electric excitation generator having a predetermined oscillation frequency. The distinctive feature of the device lies in the fact that the transducer is of the half-wave type and comprises a flat plate of piezoelectric material; a first face of said plate is provided with a set of concentric annular grooves having a uniform pitch in the vicinity of the wavelength of said radiation in water; the annular radiating zones bounded by the grooves of said plate are fitted with electrodes placed in contact with said faces; said electric generator comprises an array of adjustable phase-shifting means for supplying said electrodes at least to a partial extent with voltages having adjustable phases for focusing said radiation in the biological tissues which are acoustically coupled with said face.

Other features of the invention will be more apparent upon consideration of the following description and accompanying drawings, wherein.

Figure 1:
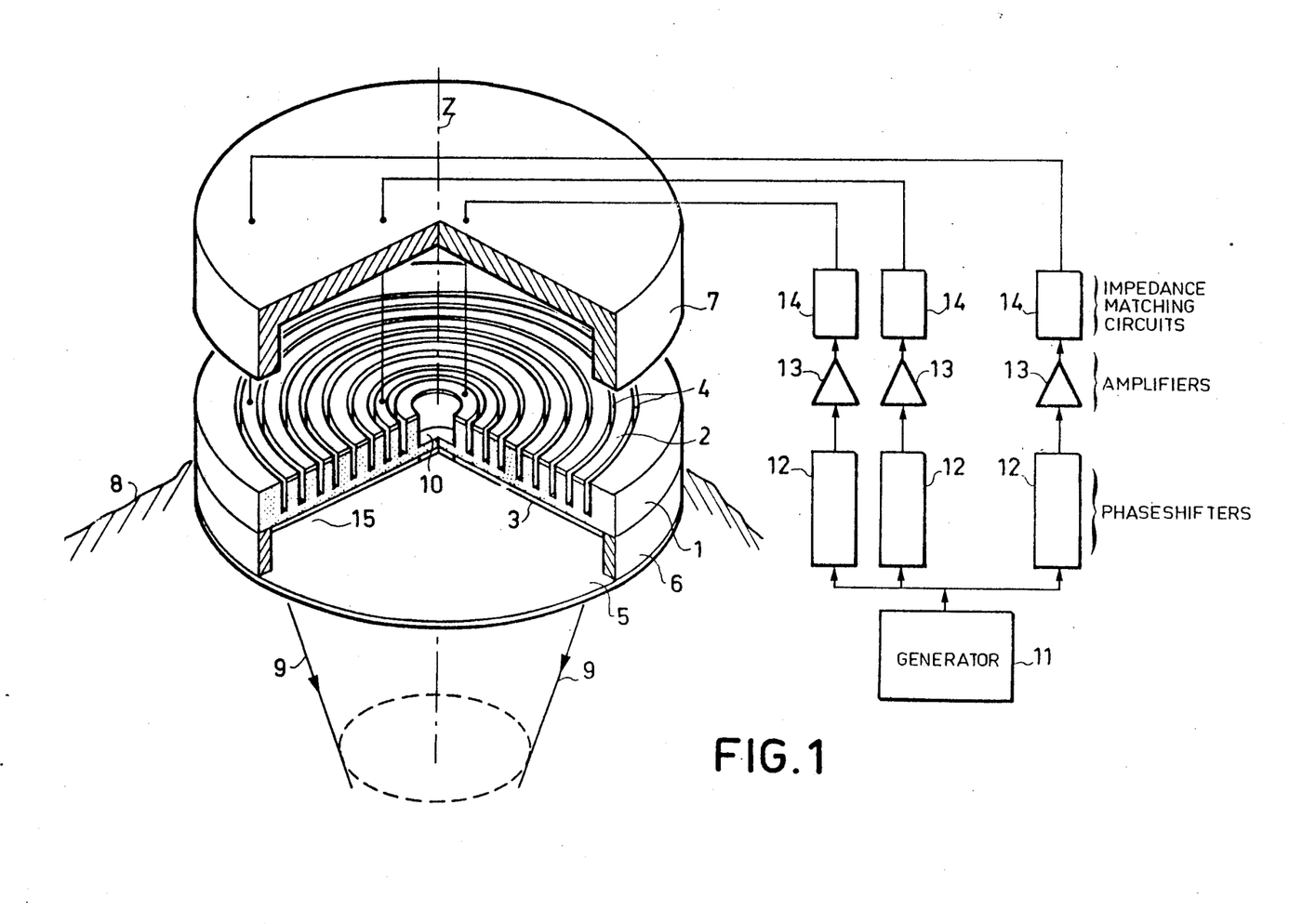
FIG. 1 is a partial isometric view of an applicator unit according to the invention.

There is shown in FIG. 1 an ultrasonic radiation device which serves to obtain localized heating of biological tissues. The device is composed of electrical excitation means shown on the right-hand side of FIG. 1 and of an applicator as shown in the partial exploded view on the left-hand side of FIG. 1. The applicator is an electromechanical transducer which is applied against the surface 8 of a body in order to radiate a focused ultrasonic beam 9 into the body. Transmission of ultrasonic waves into biological tissues underlying the surface 8 is produced by means of a plate 1 of piezoelectric material 1 cut in the shape of a disk. The distance e between the parallel circular faces of the plate 1 is chosen so as to ensure that the transducer operates in the half-wave vibrational mode at the excitation frequency $f_o$. We therefore have: $e = (v/2f_o)$, where v is the phase velocity of the ultrasonic waves within the piezoelectric material. Postulating a propagation velocity $v = 4000$ m.s$^{-1}$ and an ultrasonic emission at a frequency of 1 MHz, then in the case of piezoelectric material such as ceramic material, the resultant plate thickness is of the order of 2 mm.

According to a characteristic feature of the invention, the focused ultrasonic radiation 9 is radiated by the flat bottom face of the plate 1 which is covered with a metallization layer 3. According to a further characteristic feature of the invention, the smooth radiating face 3 is coupled with a diaphragm or membrane 5 by means of a liquid having the acoustic impedance of the biological tissues to be subjected to ultrasonic irradiation, said membrane being applied against the surface 8. A circular frame 6 attached to the plate 1 serves as an edge support for the membrane 5 which advantageously consists of a flexible film. A leak-tight cavity 15 is thus formed in front of the smooth radiating face of the plate 1. The liquid with which said cavity 15 is filled can advantageously consist of water and the bag thus formed prevents distortion of the ultrasonic wavefronts radiated by the plate 1. The water bag also performs the function of heat dissipator since it is essential to remove the heat generated within the plate. Provision can be made for circulation of the liquid in conjunction with an external heat sink connected by means of ducts (not shown in FIG. 1). Taking into account the half-wave vibrational mode of the plate 1, the acoustic impedance which is coupled with the top face 2 of said plate must be negligible compared with the acoustic impedance of the piezoelectric ceramic material. This low acoustic impedance is advantageously obtained by means of a cover 7 fitted on the top face 2 of the plate 1 and containing an air layer.

In order to emit focused ultrasonic radiation from a flat radiating face, steps must accordingly be taken to ensure that a plurality of concentric annular zones of said face radiate waves which are phase-shifted in accordance with a law which introduces phase shifts as a function of the mean radius of said zones. To this end, a plurality of annular grooves 4 are cut in the plate 1 to a depth which can attain 90% of the thickness e of said plate 1. Each ring of piezoelectric material thus formed between two successive grooves 4 constitutes an elementary ultrasonic source which is suitably decoupled from the adjacent grooves. An annular metallization layer 2 cooperates with the metallization layer 3 in order to produce an electric-field excitation of each emissive annular zone. The supply of elementary ultrasonic sources is effected by means of an a.c. voltage generator 11 which delivers an a.c. voltage having a frequency $f_o$ to an array of adjustable phase-shifters 12. The phase-shifted voltages delivered by the phase-shifters 12 are amplified by an array of variable-gain amplifiers 13. An array 14 of impedance-correcting and matching circuits connected between each metallization layer 2 and the metallization layer 3 serve to compensate for the reactive portion of the electrical impedance of each elementary piezoelectric source while also having an impedance-matching function if necessary. The output terminals of the amplifiers 13 are therefore loaded by the resistive portion of said electrical impedance, thus ensuring optimum transfer of excitation power.

In FIG. 1, the metallization layer 3 performs the function of a backing-electrode which is connected to the common electrical ground of the correcting circuits 14 and power amplifiers 13.

In order to ensure that focusing of the ultrasonic radiation 9 takes place without sidelobes, the pitch of the grooves 4 must not be substantially different from the wavelength of the ultrasonic radiation in water. Since the velocity of propagation of ultrasonic waves in water is in the vicinity of 1500 m/sec, it is apparent that the pitch p is of the order of 1.5 mm in respect of an emission frequency of 1 MHz. As a general rule, it is an advantage to reduce the number of elementary sources to a minimum in order to simplify the construction of the electrical excitation means, thus entailing the need to choose the longest pitch conducive to suppression of sidelobes. The radial width of the elementary annular sources is chosen so as to be as close as possible to the pitch p in order to obtain the maximum radiating surface area. The foregoing indications being taken into account, it is apparent that the ratio $l/e$ will be in the vicinity of 0.75 in the case of the piezoelectric ceramic material. In practice, the ratio $l/e$ can be chosen so as to prevent the multiple resonance modes which will be liable to appear with the fragmented configuration of the plate 1. In fact, the elementary transducers may not resonate solely in the thickness mode and the optimum value must be chosen by also taking into account the electromechanical coupling coefficient. This makes it necessary to choose the ratio $l/e$ between the limits of 0.5 and 1.

In order to ensure that the central operating frequency of each elementary source corresponds as exactly as possible to the excitation frequency $f_o$, a constant width 1 is adopted for all the radiating rings. This type of transducer therefore differs substantially from an emitter grating designed in accordance with the Fresnel zone theory since the radial width of the emissive zones in the latter instance vary from the center to the periphery of the grating.

Figure 2:
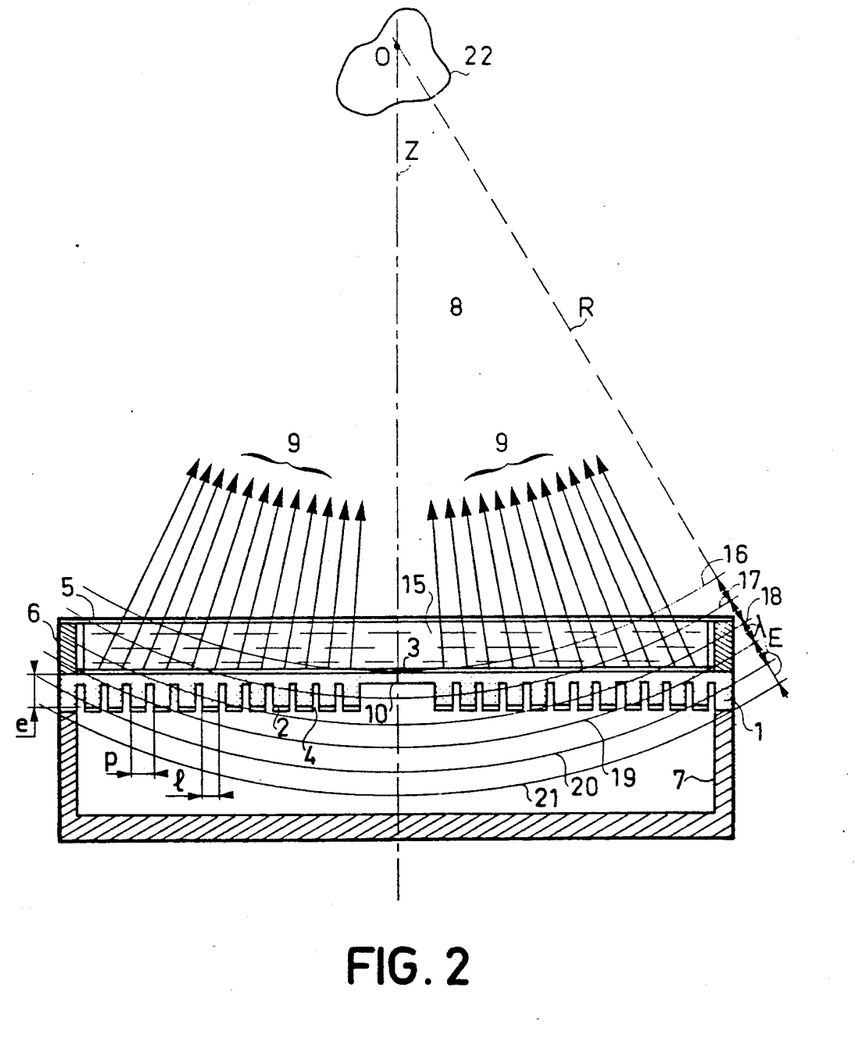
FIG. 2 is a central sectional view of the applicator of FIG. 1.

The central sectional view of FIG. 2 corresponds to the applicator of FIG. 1. The same references designate the same elements; more particularly, there is shown at the center of the plate a central recess 10 which preferably does not take part in the ultrasonic emission although the operation with a central transducer comes within the scope of the invention. The sectional view of FIG. 2 shows the biological tissues 8 subjected to ultrasonic irradiation such that the rays 9 converge to a point O of a zone 22 to be selectively heated. The focal point is assumed to be located on the axis of revolution Z of the emitting structure. In order to illustrate the phase shifts which are essential in order to emit an ultrasonic beam focused at O, there have been drawn in FIG. 2 a number of spherical equiphase wavefronts 16, 17, 18, 19, 20 and 21. The distance between said wavefronts 16 to 21 is $\lambda_E$, which is the wavelength of the ultrasonic waves within the medium 8. Said wavefronts have a common phase center at O. The wavefront 16 has a radius of curvature R which is tangent to the emissive face 3 of the piezoelectric transducer. The wavefront 17 represents a phase lag of $2\pi$ radians, the wavefront 18 represents another phase lag of $2\pi$, and so on. Considering as a phase reference the first radiating ring starting from the center of the face 3, there can be read from FIG. 2 the mean phase-lead values which must be given to the excitation voltages to be applied to the electrodes 2 in order to obtain convergence at O. It is apparent that the seventh ring starting from the center can be excited in phase with the first ring and also with the tenth ring. As the distance from the center becomes greater, so the phase lead must increase more rapidly. In fact, the phase shift is varied in sudden jumps in order to obtain an approximation of the spherical wavefront in steps. This approximation is less accurate as the distance from the center increases and as the width 1 is greater with respect to $\lambda_E$. Care should be taken to ensure that a phase error of $\pi/2$ radian in the width of the ring is not exceeded. As a function of the angular aperture of the beam, this will determine the width 1 of each radiating ring. The flexible film 5 can be applied in intimate contact with the surface of the body 8 without giving rise to disturbing refraction at the interface between the liquid 15 and the biological tissues since the acoustic velocities are equal. The flexible film 5 can advantageously consist of a thin polymer film, thus preventing impedance mismatch which would be liable to give rise to a reflection of the radiation 9.

The multiple annular transducer of FIGS. 1 and 2 can be excited in different ways. It is possible, for example, to provide acoustic power per unit area of uniform value. This can readily be obtained in the case of emitter rings having a constant width 1 since the adjusted value of impedance between the metallization layer 3 and the metallization layer 2 is inversely proportional to the mean radius of the ring. Since the radiating surface area is proportional to the radius, it will only be necessary to apply the same excitation voltage to all the rings. As will readily be apparent, the amplitude weighting technique may be utilized in order to give the ultrasonic irradiation a particular distribution at the focus. Adjustments of the excitation voltage are obtained by modifying the gain of the amplifiers.

Figure 4:
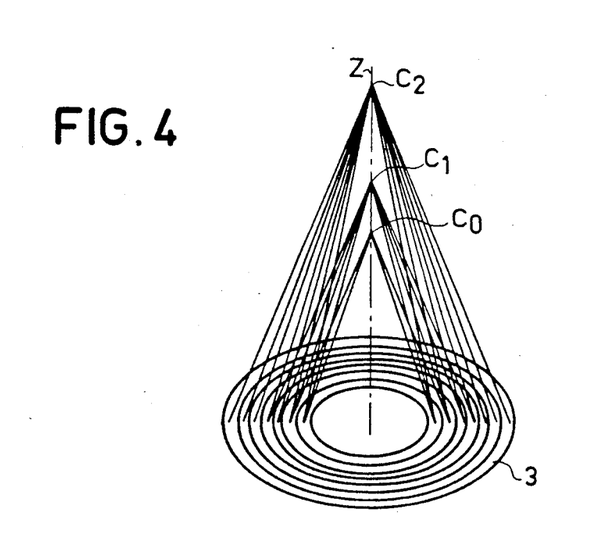

So far as phase adjustments are concerned, in order to obtain point focusing, it has been seen that the ultrasonic waves radiated by the annular sources must reach the desired focus in phase. In FIG. 4, this focusing is illustrated in the case of three foci $C_0$, $C_1$ and $C_2$ in which the angular aperture of the beam is maintained. This result is readily obtained by adapting the phase law and by using a greater or lesser number of radiating rings. In FIG. 4, focusing at $C_0$ entails the need for two central radiating rings but focusing at $C_2$ makes use of all the rings of the emissive face 3. In order to obtain a constant angular aperture, the number of rings varies in proportion to the projection distance.

This technique makes it possible to maintain unchanged dimensions at the heating zone both in width and in depth. Since the number of rings employed is in that case proportional to the depth, there is thus achieved a compensation for the loss of power resulting from attenuation of propagation.

Figure 5:
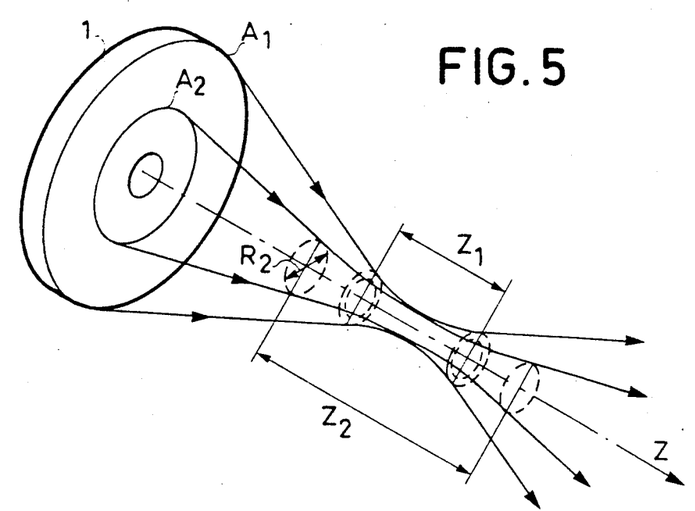

Operation with a greater or lesser number of radiating elements makes it possible to vary the angular aperture of an ultrasonic beam which is focused at a predetermined distance. FIG. 5 illustrates a piezoelectric plate having a radiating face $A_1$. When all the annular transducers composing said face are excited, focusing takes place along the normal projection axis Z. In the transverse direction, distribution of the ultrasonic intensity is governed by the diffraction laws of an annular aperture. In the longitudinal direction, the heating zone has a depth $Z_1$ corresponding to the depth of field. By reducing the active face at the zone $A_2$, it is apparent that the depth $Z_2$ and the width $R_2$ of the heating zone have increased in respect of the same depth of focus.

It is useful to recall the formulae relating to a circular aperture. The width at $-3$ dB of a focused beam is approximately equal to $(\lambda \cdot F)/(D)$ where $\lambda$ is the wavelength, F is the focal distance and D is the diameter of the emissive surface of the ultrasonic radiation. The depth of field at $-3$ dB has a value which is substantially $7.14 \lambda (F/D)^2$.

Figure 3:
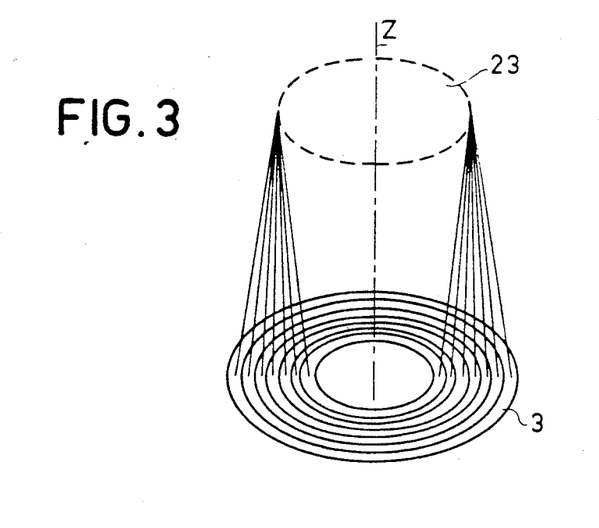
FIGS. 3 to 5 are explanatory diagrams.

Another method of focusing ultrasonic radiation is shown in FIG. 3. This method consists in exciting the rings of the radiating face 3 with a phase law which causes the emitted waves to be in phase coincidence on a circular focal line 23. This technique makes it possible to enlarge the heated zone or to heat solely the periphery of a tumor.

It is apparent from the foregoing that the device for selective heating by ultrasonic waves whose structure and operation are illustrated in FIGS. 1 to 5 has considerable flexibility of adjustment while utilizing a flat radiating surface as an ultrasonic emitter. Adjustment in amplitude and weighting of the sources is readily performed at the level of the power amplifiers 13 which have a gain control. Conditions of focusing on the axis Z or about the axis Z are adjusted at the level of the phase-shifters 12. By way of example but not in any limiting sense, use can be made of RC phase-shifters which retain the amplitude and are electrically controlled by variation of the RC product. As has already been noted, localized heating is dependent on the phase and amplitude characteristics of the excitation voltages applied to a more or less large number of elementary annular emitters. The generator 11 is capable of delivering a sinusoidal a.c. voltage or a succession of wave trains which are more or less close together, thus adding a further possibility of heating adjustment. By programmed control of the excitation means, it is also possible to carry out zone scanning both in depth and in width in order to spread the heating effect. Finally, it is possible to employ a plurality of applicators for emitting coherent and convergent radiations in order to improve localization of the heating.

Figure 6:
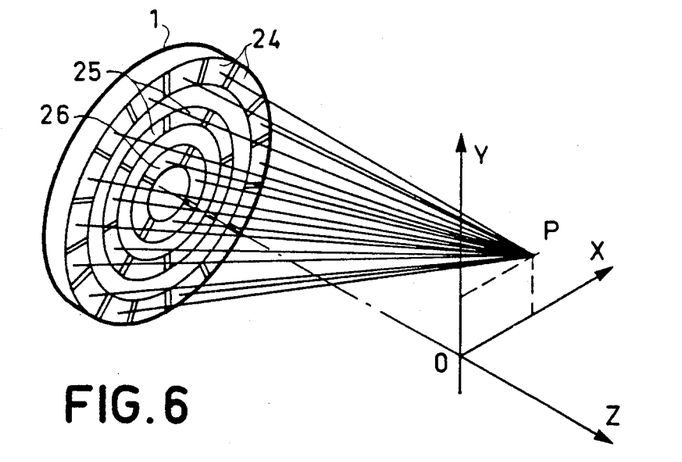
FIG. 6 shows an alternative embodiment of the applicator unit of FIG. 1.

FIG. 6 illustrates a further possibility offered by the device according to the invention. Each radiating ring of the plate 1 can in fact be subdivided into angular sectors 24, 25 and 26 by means of segmented metallization layers 2 which are capable of cooperating if necessary with radial grooves. The subdivision of the rings increases from the center to the periphery as shown in FIG. 6 in order to maintain the frequency response of the elementary piezoelectric emitters accurately centered on the selected emission frequency. The elementary emitters 24, 25, 26 are connected to amplifiers 13 via impedance-matching circuits 14. Not only does a greater number of phase-shifters 12 make it possible to produce a phase-shift law so as to permit focusing of the emission at a point P of the plane XOY but this law can also comprise a phase-shift distribution, the extent of which determines the coordinates of the point P in the plane XY. It therefore becomes possible to address any point of the volume determined by the system of coordinates XYZ and to produce a time-dependent variation of this address if so desired. In addition to this possibility, consideration could also be given to amplitude modulation or pulse modulation of the generator 11, thus permitting additional regulation of the heat intensity.

The technique of ultrasonic heating which has just been described has shown that the central circular zone of the piezoelectric plate 1 need not be employed as a heating emitter. This zone can accordingly serve to accommodate a set of means for emission and reception of ultrasonic waves of shorter wavelength in order to permit visual display of biological tissues during treatment by hyperthermia.

Figure 7:
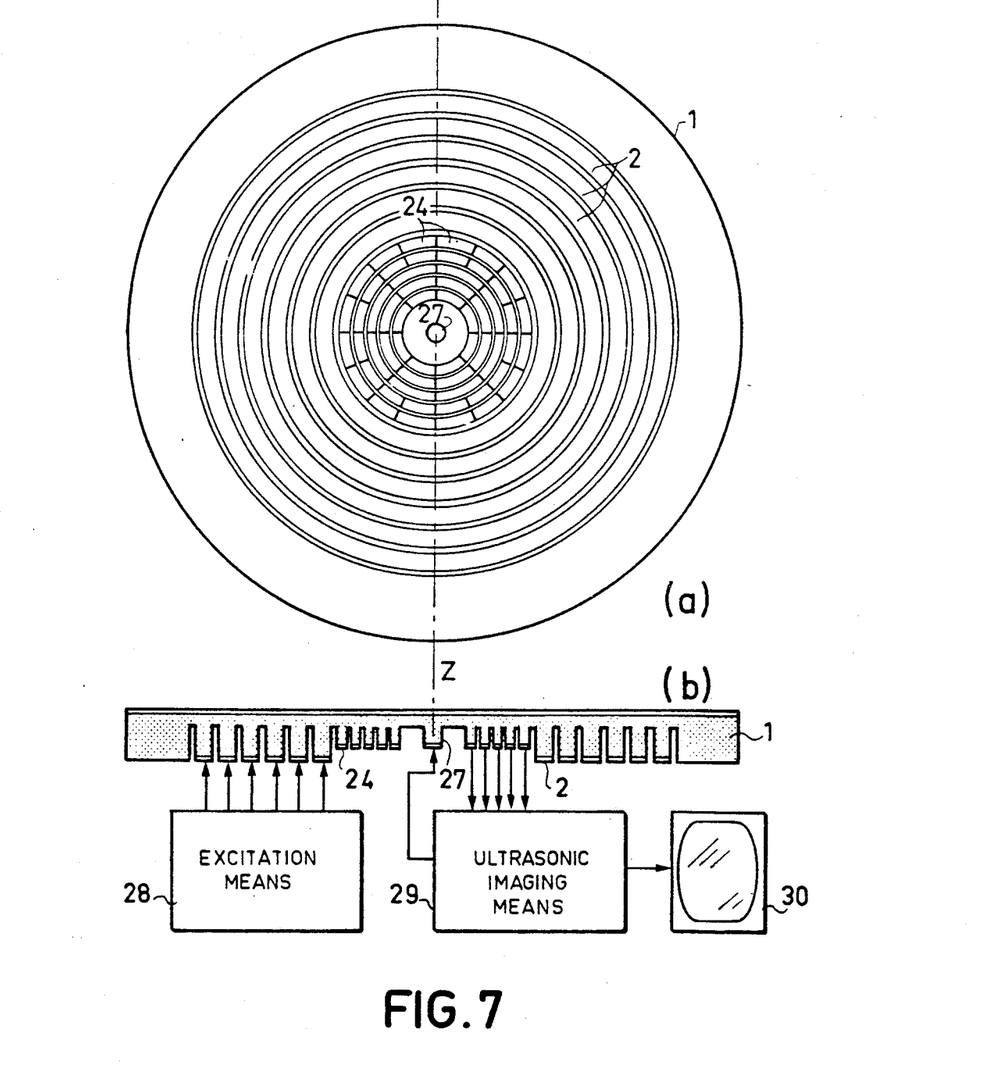
FIG. 7 illustrates another alternative embodiment of the unit of FIG. 1.

This possibility is illustrated in the bottom view of FIG. 7(a) and in the central sectional view of FIG. 7(b). As in FIGS. 1 and 2, there are again shown a piezoelectric plate 1 carrying a concentric array of annular metallization layers 2 separated by equidistant grooves. The metallization layers 2 are connected to an excitation unit 28 in which the electric circuits of FIG. 1 and their control means are grouped together. This accordingly constitutes an ultrasonic heating system of the type described earlier. By way of example, this system is completed in the central portion of the plate 1 by an ultrasonic display system in which the transducer elements 24 and 27 benefit by the same technology apart from the fact that they are of smaller size in order to operate at higher frequency and with reduced power. However, provision can be made for an imagery transducer array which is entirely formed in another piezoelectric plate. More specifically and by way of non-limitative example, a central transducer element provided with an excitation electrode 27 emits ultrasonic radiation at 3 MHz, for example, this radiation being applied to the field within which the biological tissues are to be visually displayed. An ultrasonic imaging unit 29 delivers ultrasonic pulses to the central transducer 27, thus producing echoes which are picked-up by the array of receivers 24 (these receivers may or may not be sectoral). The unit 29 receives a series of signals returned by the electrodes 24, said signals being processed as a function of the amplitude of phase and transit time so as to form a visible image of the scanned field on a monitor 30. No further details need be given in regard to the visual display system since this technique is described at great length in the known fields of sonar and echography. One point which must be mentioned, however, is that the heating has an influence on the rate of propagation of ultrasonic waves which may attain a variation of 0.1% per degree centigrade. By performing a fine measurement of the transit time, it is possible to deduce information relating to control of the temperature elevation produced. It is also possible to achieve measurement of the temperature elevation produced by considering the temperature drift of the coefficient of reflection of a tumor to be treated.

By way of conclusion, a few numerical indications will now be given in connection with a typical arrangement of an acoustic hyperthermia device.

Ultrasonic emission takes place at a frequency of 400 kHz with an acoustic power of 50 W. The irradiator is formed by a plate of piezoelectric ceramic material having a diameter of 100 mm. Said plate is made up of fourteen concentric radiation-emitting rings. Focusing can be carried out at depths within the range of 20 mm to 120 mm in order to heat a volume of a few cm$^3$. At this frequency, absorption of the ultrasonic waves by biological tissues is of the order of 0.5 dB/cm, thus ensuring good penetration on condition that neither bone tissue nor air pockets are encountered.

The foregoing description relates to devices for localized heating of biological tissues. These devices are based on projection of ultrasonic radiation by means of an applicator fitted with an electromechanical transducer which selectively irradiates the region to which the hyperthermia treatment is applied. The region to be treated is selected by means of a focusing process entailing the use of a set of concentric radiating elements associated with phase-shifting means. The biological tissues located upstream and downstream of the focal point at which the ultrasonic radiation meets undergo progressively lower temperature elevation as the distance from the focal point increases. The problem which arises is to adapt the radiation intensity at the focal point to the shape of the volumes to be heated while taking into account the heat losses caused by vascularization and thermal conduction.

The irradiation means described earlier comprise a disk of piezoelectric material subdivided into concentric radiating half-wave elements by annular grooves formed in the rear face at uniform intervals from the center to the periphery of the disk. By subjecting an appreciable number of radiating elements to electrical excitation with suitably phase-shifted alternating-current signals, it is possible to project ultrasonic radiation onto a pointlike or annular focus so as to produce localized heating. In order to ensure uniform heating in a region which is being treated, it has been suggested that, by modifying the phase law which establishes the location of the focus, heating can be applied successively to a number of different sites of any one region to be treated. Modification of a phase law, however, is a relatively complex undertaking and it is often preferable for this reason to utilize a plurality of foci which are irradiated simultaneously when it is proposed to treat a relatively extensive region or a number of diseased areas of an organ of substantial volume. It is possible in this case to utilize a number of the aforementioned applicators at the same frequency in order to surround a tumoral volume or a group of tumors.

Figure 8:
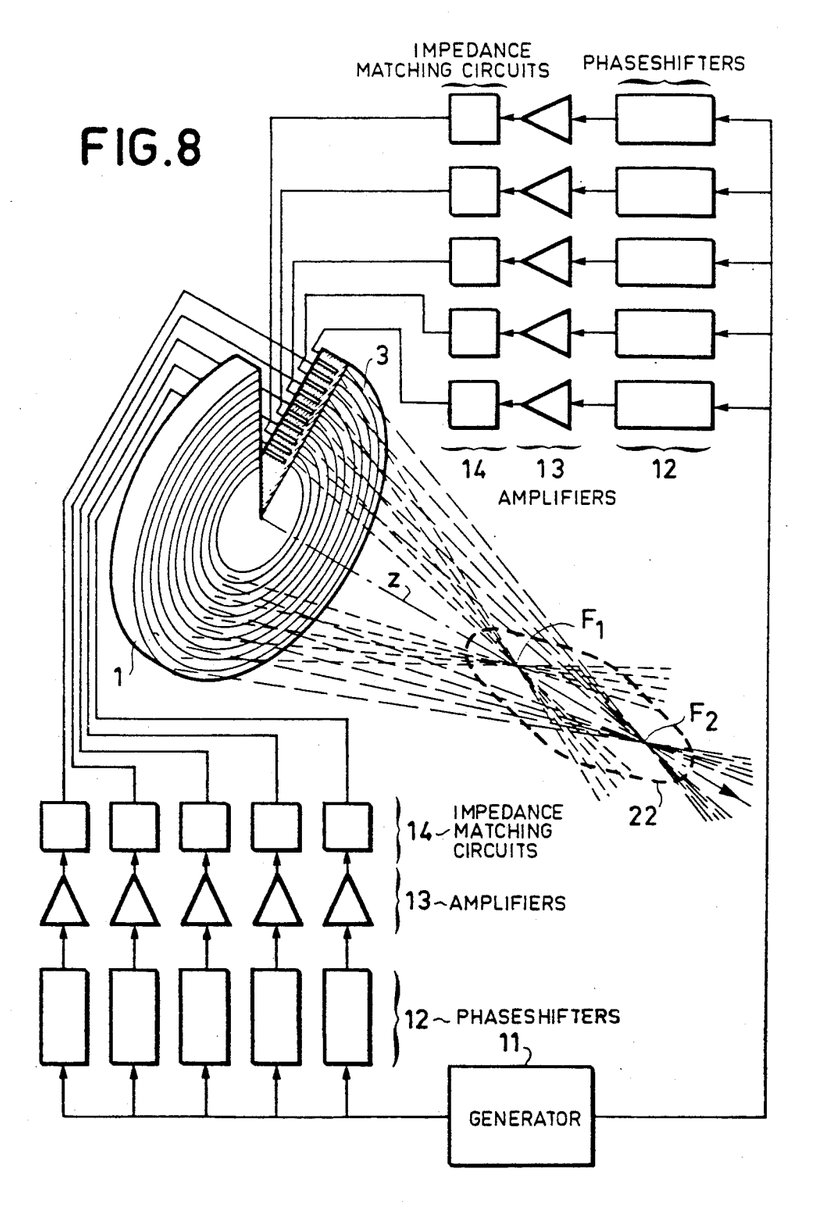
FIG. 8 is an isometric view of a heating device according to the invention.

FIG. 8 shows an electromechanical transducer composed of a piezoelectric plate 1 having two flat principal faces covered with excitation electrodes. The front face 3 is completely covered by a ground electrode. The rear face which is visible in FIG. 8 through the cutaway sector comprises approximately ten concentric annular electrodes located between annular grooves formed in the piezoelectric plate 1. Uniform spacing of the grooves is adopted in order to define an array of concentric transducers which all operate in the half-wave vibrational mode at the excitation frequency chosen for ultrasonic emission. The elementary emissive zones are defined in FIG. 8 by circles located at the level of the grooves but these boundary lines are shown only in order to gain a better understanding since the radiating face 3 is in fact smooth.

Electrical excitation of the transducer of FIG. 8 is effected by means of a generator 11 which delivers an alternating-current voltage of predetermined frequency. The connection between said generator 11 and the electrodes of the rear face of the transducer 1 is established by two groups of five channels which are connected respectively to the even-numbered electrodes and to the odd-numbered electrodes. Each channel comprises an adjustable phase-shifting circuit 12, a variable-gain amplifier 13 and an impedance-matching circuit 14. The rear face of the transducer 1 is coupled to a medium having low acoustic impedance and serving by wave reflection to produce maximum radiation via the face 3 of the transducer. Said face 3 is coupled to the biological tissues to be irradiated by means of a water bag (not shown in the drawings) which does not have any marked refracting action on the ultrasonic beams emitted by the face 3.

The excitation group 12-13-14 shown in the lower portion of FIG. 8 is adjusted in amplitude and in phase so as to ensure that the first, third, fifth, seventh and ninth radiating annular zones counted from the center project a first ultrasonic radiation onto the focal point $F_1$. The excitation group 12-13-14 shown in the upper right-hand portion of FIG. 8 is adjusted in amplitude and in phase so as to ensure that the second, fourth, sixth, eighth and tenth radiating annular zones project a second ultrasonic radiation onto a second focal point $F_2$. These focal points occupy separate and distinct positions on the axis Z so as to apply uniform heating to a tumoral volume 22 which is elongated in the direction of said axis.

Without thereby departing from the scope of the invention, provision can be made for more than two groups of radiating zones in order to obtain more than two focal points along the axis Z. A predetermined number of focal points can be located outside the axis Z in order to provide enhanced uniformity of heating of the tumoral volume 22.

It is observed in FIG. 8 that the angular aperture of the beam which converges to the focal point $F_1$ is larger than that of the beam which converges to the focal point $F_2$. On the other hand, the power outputs which reach these two focal points are substantially the same since said outputs are produced by surfaces which are approximately similar. Losses in diffraction and depth of field being taken into account, it is apparent that the heating is more localized and has higher intensity at the focal point $F_1$ than at the focal point $F_2$.

Figure 9:
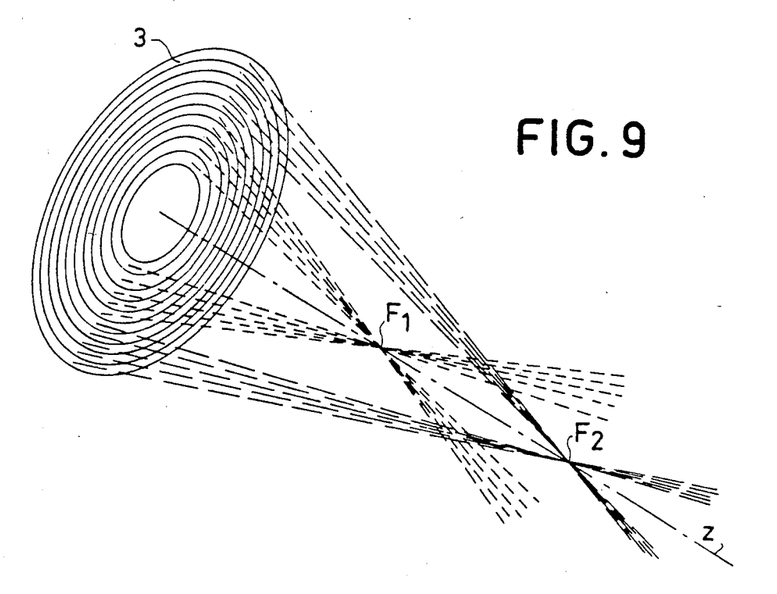
FIG. 9 illustrates a first alternative embodiment of the projection mode according to FIG. 8.

FIG. 9 illustrates an alternative embodiment of the device according to the invention in which consideration is given solely to essential features, namely to the radiating annular zones of the transducer face 2 and to the ultrasonic beams, the coherent addition of which takes place at the focal points $F_1$ and $F_2$. The excitations provided by the two groups of FIG. 8 are applied respectively to the five contiguous electrodes located nearest the center and to the five contiguous electrodes which are farthest away from the center. Thus the emitted power at the nearest focal point $F_1$ is of lower value than the emitted power at the focal point $F_2$. On the other hand, the angular apertures of the two projected beams can be adjusted so as to produce temperature elevations of equal intensity by relying on the effects of diffraction, losses and depth of field. Since the two emissions are not inter-related but separated into two wholly distinct zones, enhanced decoupling is consequently achieved.

Figure 10:
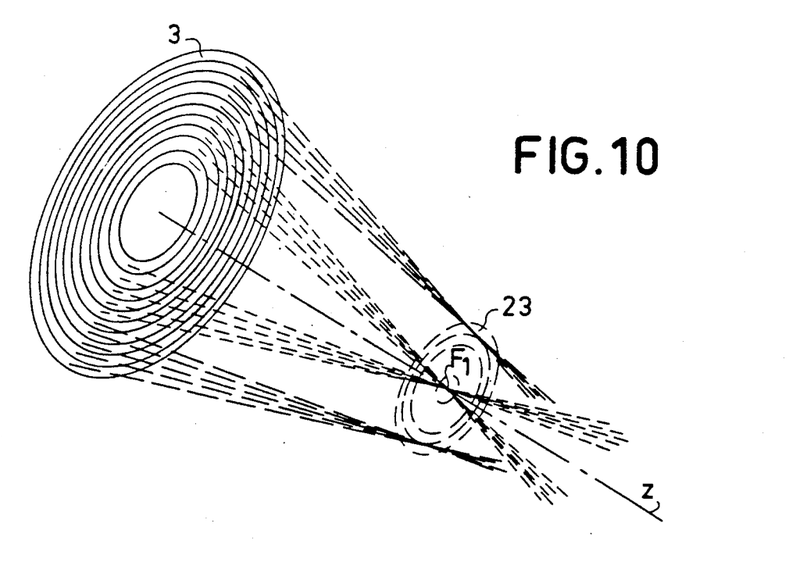
FIG. 10 illustrates a second alternative embodiment of the projection mode according to FIG. 8.

By changing the phase law applied to the excitation of the five peripheral annular zones of FIG. 9, steps can accordingly be taken to ensure that the focal point $F_2$ is a ring-shaped focus 23 which can surround the focal point $F_1$. This variant is illustrated in FIG. 10. It is apparent that this arrangement of a focal point surrounded by an annular focus makes it possible to irradiate a tumoral volume having a flattened shape in the direction of the axis Z.

Generally speaking, the device described in this application with reference to FIGS. 8 to 10 offers greater flexibility by virtue of the combinations which can be achieved with simultaneous projections onto point-type or annular foci.

It has been assumed in the foregoing that the two excitation groups 12, 13 and 14 are supplied by the same generator 11. This solution calls for a single ultrasonic emission frequency, with the result that interaction of the beams is liable to produce inhomogeneity arising from the stationary interference fringes. In order to overcome this disadvantage, it is proposed to supply the excitation groups 12, 13, 14 of FIG. 8 with alternating-current signals having slightly differentiated frequencies, these signals being produced by two frequency-shifted oscillators contained within the generator 11. The frequency shift can be small while ensuring sufficient mobility of the fringes to ensure uniform ultrasonic irradiation. Half-wave operation of the radiating elements can be ensured under good conditions by means of a piezoelectric plate of constant thickness since accurate tuning can be subjected to fine adjustment by modifying the width of the annular grooves which are formed in the rear face of the plate and serve to delimit the radiating elements.

What is claimed is:

1. A device for localized heating of biological tissues comprising:
    electromechanical transducer means for projecting ultrasonic radiation, coupled to an electric excitation generator having a predetermined oscillation frequency, said transducer means being of the half-wave type and comprising a rigid plate of piezoelectric material, a first face of said plate being provided with a set of concentric annular groves of uniform pitch in the vicinity of the wavelength of said radiation in water, a second face of said plate being smooth and flat,
    said plate having annular radiating zones bounded by said grooves and provided with electrodes placed in contact with said faces, each annular radiating zone describing a circle to obtain a circular radiation pattern; and
    an electric excitation generator having a predetermined oscillation frequency, said generator including an array of adjustable phase-shifting means for supplying said electrodes at least partially with voltages having adjustable phases for selectively focusing said radiation into biological tissues which are acoustically coupled with said second face, said selective focusing including moving said radiation pattern in a direction orthogonal to said plate.

2. A device according to claim 1, wherein:
    said second face is covered by a bag which is permeable to said radiation and filled with a liquid having an acoustic impedance whose value is closely related to the acoustic impedance of water.

3. A device according to claim 1 or claim 2, wherein:
    the face of the piezoelectric plate in which grooves are formed is fitted with a cover containing a medium having an acoustic impedance of negligible value compared with the acoustic impedance of said piezoelectric material.

4. A device according to claim 1 or claim 3, wherein the piezoelectric plate is provided at the center of said plate with ultrasonic transducer means in cooperating relation with a visual display system used to monitor the irradiated zone and to control the degree of heating, said visual display means being utilized for emission and reception of ultrasonic radiations having a higher frequency than said predetermined frequency.

5. A device according to claim 1, wherein said annular radiating zones radiate in sectors with phase-shifted electrical excitations which permit transverse scanning of the focused beam.

6. A device according to claim 1, wherein:
    the electrical excitation of said annular radiating zones is phase-shifted so as to focus said radiation in a closed circular contour.

7. A device according to claim 1, wherein:
    said piezoelectric material is a piezoelectric ceramic material metallized on both faces.

8. A device according to claim 7, wherein:
    the ratio of the width of said annular radiating zones to the thickness of said plate is within the range of 0.5 to 1.

9. A device according to claim 1, wherein:
    the emission of ultrasonic radiation is continuous emission.

10. A device according to claim 1, wherein:
    the emission of ultrasonic radiation is pulsed emission.

11. A localized heating device according to claim 1, wherein the radiating zones of one and the same piezoelectric plate form N emitting groups excited by voltages in which the phases ensure simultaneous projection of N ultrasonic radiations onto N separate and distinct focal points.

12. A device according to claim 11, wherein the phases of said voltages are chosen so as to ensure that at least one of the N ultrasonic radiations is brought to a point focus.

13. A device according to claim 11, wherein the phases of said voltages are chosen so as to ensure that at least one of the N ultrasonic radiations is brought to an annular focus.

14. A device according to claim 11, wherein the frequencies of said ultrasonic radiations are differentiated.

15. A device according to claim 11, wherein the ultrasonic radiations emanate from inter-related radiating annular zones.

16. A device according to claim 11, wherein at least one of the ultrasonic radiations emanates from an emissive area comprising a plurality of contiguous annular zones.

17. A device according to claim 1 wherein said radiation pattern is a point.

18. A device according to claim 1 wherein said selective focusing includes focusing said radiation to substantially a single point in said biological tissues.

19. A device according to claim 1 wherein said selective focusing includes focusing said radiation to substantially a first focal point and a second point in said biological tissues.

20. A device according to claim 19 wherein said first and second focal points are co-linear with a line orthogonal to said plate.

21. A device according to claim 1 wherein said selective focusing includes focusing said radiation at a plurality of focal points in said biological tissues.

22. A device according to claim 1 wherein each said annular radiating zone is divided into a plurality of elementary radiators, each being individually excited by said electric excitation generator, and wherein said selective focusing includes moving said radiation pattern in a direction of substantially parallel to said plate.

23. A device according to claim 1 wherein said selective focusing includes focusing said radiation into a focal point and into a radiation pattern having a closed circular contour.

24. A device according to claim 1 further including:
    imagery transducer means, abutting said annular radiating zones, for transmitting radiation to and receiving radiation from said biological tissues and for providing and image signal containing imaging information about said biological tissues; and
    imaging means for receiving said image signal and providing an output signal from which an image of said biological tissues is derived.

25. A device according to claim 24 further including display means, coupled to said imaging means, for displaying an image of said biological tissues.

26. A device according to claim 24 wherein said imagery transducer means includes an array of annular imaging radiation zones which are substantially concentric with said annular radiating zones.

27. A device according to claim 26 further including an excitation electrode, arranged substantially concentric with said annular imaging zones, for transmitting ultrasonic radiation into said biological tissues.

* * * * *